(12) United States Patent
Cho et al.

(10) Patent No.: US 8,940,538 B2
(45) Date of Patent: Jan. 27, 2015

(54) APPARATUS AND METHOD FOR QUANTIFYING BINDING AND DISSOCIATION KINETICS OF MOLECULAR INTERACTIONS

(75) Inventors: Hyun Mo Cho, Daejeon (KR); Gal Won Che, Daejeon (KR); Yong Jai Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 294 days.

(21) Appl. No.: 13/511,330

(22) PCT Filed: Oct. 29, 2010

(86) PCT No.: PCT/KR2010/007502
§ 371 (c)(1),
(2), (4) Date: May 22, 2012

(87) PCT Pub. No.: WO2011/062377
PCT Pub. Date: May 26, 2011

(65) Prior Publication Data
US 2012/0295357 A1  Nov. 22, 2012

(30) Foreign Application Priority Data
Nov. 23, 2009  (KR) .................. 10-2009-0113164

(51) Int. Cl.
*G01N 21/21* (2006.01)
*G01N 21/05* (2006.01)
(Continued)

(52) U.S. Cl.
CPC ........ *G01N 21/211* (2013.01); *B01L 3/502715* (2013.01);
(Continued)

(58) Field of Classification Search
CPC .............. B01L 3/502715; B01L 2300/0627; B01L 2300/0654; B01L 2400/086; G01N 21/05; G01N 21/21; G01N 21/211; G01N 21/41; G01N 21/55; G01N 33/53; G01N 33/5302; G01N 33/543; G01N 33/551; G01N 33/552; G01N 33/557; G01N 2021/056; G01N 2021/21; G01N 2021/211; G01N 2021/213; G01N 2021/214; G01N 2021/215; G01N 2021/41; G01N 2021/55; G01N 2033/53
USPC ........... 422/82.05, 82.09, 401–404, 408, 412, 422/425, 430, 501–502, 507; 436/34, 436/85–87, 94–95, 164–165, 171, 518, 524, 436/527
See application file for complete search history.

(56) References Cited

U.S. PATENT DOCUMENTS 4,508,832 A * 4/1985 Carter et al. .................. 436/517
4,521,522 A * 6/1985 Lundstrom et al. ........... 436/525
(Continued)

FOREIGN PATENT DOCUMENTS

KR    100742982 B1    7/2007
KR    100808274 B1    2/2008

OTHER PUBLICATIONS

Vroman, L. et al, Surface Science 1969, 16, 438-446.*
(Continued)

*Primary Examiner* — Arlen Soderquist
(74) *Attorney, Agent, or Firm* — Allen, Dyer, Doppelt, Milbrath & Gilchrist, P.A.

(57) ABSTRACT

The present invention relates to an apparatus for quantifying the binding and dissociation kinetics of molecular interactions of small molecular bio materials with high sensitivity almost without the influence of a change in the reflective index resulting from a buffer solution by making polarized incident light incident on the binding layer of a bio material, formed in a thin dielectric film, so that the polarized incident light satisfies a p-wave non-reflecting condition and a quantifying method using the same.

17 Claims, 8 Drawing Sheets

(52) U.S. Cl.
CPC .... *B01L 2300/0654* (2013.01); *B01L 2400/086* (2013.01)
USPC ....... 436/34; 422/82.05; 422/82.09; 422/401; 422/402; 422/403; 422/404; 422/408; 422/412; 422/425; 422/430; 422/501; 422/502; 422/507; 436/85; 436/86; 436/87; 436/94; 436/95; 436/164; 436/165; 436/171; 436/518; 436/524; 436/527

(51) Int. Cl.
*G01N 33/53* (2006.01)
*B01L 3/00* (2006.01)

(56) References Cited

U.S. PATENT DOCUMENTS

| | | | |
|---|---|---|---|
| 4,537,861 A * | 8/1985 | Elings et al. | 436/518 |
| 4,873,430 A * | 10/1989 | Juliana et al. | 250/225 |
| 4,908,508 A * | 3/1990 | Dubbeldam | 250/225 |
| 4,957,368 A * | 9/1990 | Smith | 356/369 |
| 5,164,589 A * | 11/1992 | Sjodin | 250/227.24 |
| 5,166,752 A * | 11/1992 | Spanier et al. | 356/369 |
| 5,172,182 A * | 12/1992 | Sting et al. | 356/244 |
| 5,313,264 A * | 5/1994 | Ivarsson et al. | 356/73 |
| 5,402,237 A * | 3/1995 | Rhiger et al. | 356/369 |
| 5,739,910 A * | 4/1998 | Castor | 356/369 |
| 5,788,632 A * | 8/1998 | Pezzaniti et al. | 600/316 |
| 5,958,704 A * | 9/1999 | Starzl et al. | 435/7.1 |
| 5,972,612 A * | 10/1999 | Malmqvist et al. | 435/6.14 |
| 6,329,209 B1 * | 12/2001 | Wagner et al. | 506/13 |
| 6,346,376 B1 * | 2/2002 | Sigrist et al. | 435/5 |
| 6,596,545 B1 * | 7/2003 | Wagner et al. | 506/7 |
| 6,937,341 B1 * | 8/2005 | Woollam et al. | 356/436 |
| 7,008,794 B2 * | 3/2006 | Goh et al. | 436/164 |
| 7,187,446 B2 * | 3/2007 | Kimura | 356/445 |
| 7,193,703 B2 * | 3/2007 | Hakamata et al. | 356/246 |
| 7,368,292 B2 * | 5/2008 | Hummel et al. | 436/171 |
| 7,373,255 B2 * | 5/2008 | Karlsson et al. | 702/19 |
| 7,688,446 B2 * | 3/2010 | Nabatova-Gabain et al. | 356/369 |
| 7,817,266 B2 * | 10/2010 | Pfeiffer et al. | 356/246 |
| 7,879,619 B2 * | 2/2011 | Jing et al. | 436/171 |
| 2002/0110932 A1 * | 8/2002 | Wagner et al. | 436/518 |
| 2004/0005582 A1 * | 1/2004 | Shipwash | 435/6 |
| 2004/0142482 A1 | 7/2004 | Westphal et al. | |
| 2007/0082408 A1 * | 4/2007 | Jing et al. | 436/164 |

OTHER PUBLICATIONS

Stenberg, M. et al, Journal of Colloid and Interface Science 1979, 72, 255-265.*
Stenberg, M. et al, Materials Science and Engineering 1980, 42, 65-69.*
Elwing, H. et al, Journal of Immunological Methods 1981, 44, 343-349.*
Jonsson U. et al, Journal of Colloid and Interface Science 1982, 90, 148-163.*
Cuypers, P. A. et al, Journal of Biological Chemistry 1983, 258, 2426-2431.*
Jonsson U. et al, Colloids and Surfaces 1985, 13, 333-339.*
Nygren, H., Colloids and Surfaces B: Bioinerfaces 1995, 4, 243-250.*
Wahlgren, M. et al, Journal of Colloid and Interface Science 1995, 175, 506-514.*
Bain, C. D., Current Opinion in Colloid and Interface Science 1998, 3, 287-292.*
Ortega-Vinuesa, J. L. et al, Biomaterials 1998, 19, 251-262.*
Karlsson, C. A.-C. et al, Colloids and Surfaces B: Biointerfaces 2001, 20, 9-25.*
Plocinik, R. M. et al, Analytica Chimica Acta 2003, 496, 133-142.*
Ying, P. et al, Colloids and Surfaces B: Biointerfaces 2003, 32, 1-10.*
Wang, Z. H. et al, Analytical Chemistry 2003, 75, 6119-6123.*
Wang, Z. H. et al, Journal of Immunilogical Methods 2004, 285, 237-243.*
Speijer, H. et al, Analytical Biochemistry 2004, 326, 257-261.*
Poilizzi, M. A. et al, Journal of the American Chemical Society 2004, 126, 5001-5007.*
Wang, Z. H. et al, Colloids and Surfaces B: Biointerfaces 2004, 34, 173-177.*
Wang, Z. H. et al, Electrophoresis 2006, 27, 4078-4085.*
Bae et al., "Immunosensor for Detection of *Salmonella typhimurium* Based on Imaging Ellipsometry," Colloids and Surfaces A: Physiochem. Eng. Aspects, vol. 257-258, 2005, pp. 19-23.

* cited by examiner

Binding concentration

Times

Angle of incidence(°)

APPARATUS AND METHOD FOR QUANTIFYING BINDING AND DISSOCIATION KINETICS OF MOLECULAR INTERACTIONS

TECHNICAL FIELD

The present invention relates to an apparatus and method for quantifying the binding and dissociation kinetics of molecular interactions of small molecular bio materials by using an ellipsometry and a reflectometry under a liquid immersion micro flow paths environment. More particularly, the present invention relates to an apparatus for quantifying the binding and dissociation kinetics of molecular interactions of small molecular bio materials with high sensitivity almost without the influence of a change in the reflective index resulting from a buffer solution by making polarized incident light incident on the binding layer of a bio material, formed in a thin dielectric film, so that the polarized incident light satisfies a p-wave non-reflecting condition and a quantifying method using the same.

BACKGROUND ART

A reflectometry and an ellipsometry are photometic analysis technologies for finding the thickness or optical physical properties of samples by quantifying a change in the reflectivity or a polarization state of reflected light reflected from a surface of the sample and analyzing the quantified value. Quantifying equipment using the above technologies includes a reflectometer and an ellipsometer. The reflectometer and the ellipsometer are being utilized to evaluate the thin film thickness and the physical properties of various nano levels in the nano thin film manufacturing process of the semiconductor industry. Furthermore, the use of the reflectometer and the ellipsometer is expanded to the bio industry, and an attempt to analyze the interface of bio materials, such as protein, DNA, virus, and new medicine materials, is being made.

A conventional reflectometer is problematic in that it is sufficient to evaluate the thickness and the physical properties of a nano thin film of several nano meters (nm) or higher in size, but it has low reliability because of low measurement sensitivity in analyzing small molecular bio materials requiring the sensitivity of approximately 1 to 0.001 nm range. The ellipsometer has the measurement sensitivity of 0.01 nm or lower, as compared with the reflectometer. In particular, the ellipsometer has high measurement sensitivity in a condition in which the contrast of a refractive index is high as in the thickness measurement of an oxide film having a relatively low refractive index than a semiconductor formed over a semiconductor substrate of a high refractive index.

However, the ellipsometer requires a quantifying method with an improved sensitivity in order to analyze even small molecular bio materials.

A conventional technique for improving the measurement sensitivity when analyzing bio materials includes a Surface Plasmon Resonance (SPR) sensor (hereinafter referred to as an 'SPR sensor') in which the reflectometry and a surface plasmon resonance technology are mixed. A surface plasmon resonance phenomenon refers to a phenomenon in which electrons existing in a metal surface are excited by light waves and collectively vibrated in the normal direction of the surface and, at this time, light energy is absorbed. The SPR sensor has been known to be able to measure the thickness and a change in the reflective index of a nano thin film adjacent to a metal surface by using the surface plasmon resonance phenomenon sensitive to the polarization characteristic of light and also to measure a change in the binding concentration of a bio material by using a non-labeling method not using a fluorescent material in real time.

FIG. 1 is a diagram showing the construction of a conventional SPR sensor for analyzing bio materials. As shown in FIG. 1, the conventional SPR sensor chiefly includes a prism 10, a thin metal film 20, a micro flow path 30, a light source 40, a polarizer 50, an analyzer 60, and a photodetector 70. The conventional SPR sensor has the thin metal film 20, such as gold (Au) or silver (Ag), coated on one surface of the prism 10 in thickness of several tens of nm and has the micro flow path 30 formed on the thin metal film 20. Here, when a buffer solution 34 in which samples 32 of bio materials are dissolved is injected into the micro flow path 30, the bio materials are bound to ligand materials 22 formed on a surface of the thin metal film 20, thus forming a binding layer of a predetermined thickness.

Next, light generated by the light source 40 is polarized by the polarizer 50. The polarized incident light is incident on the interface of the thin metal film 20 at a Surface Plasmon Resonance angle (hereinafter referred to as an SPR angle (spr)) via the prism 10 so that it generates surface plasmon resonance is generated. Here, the reflected light reflected from the thin metal film 20 includes optical data regarding the binding layer of the samples 32. That is, in the process of the samples 32 being bound to and dissociated from the thin metal film 20, the binding and dissociation kinetics of molecular interactions, such as a binding concentration and the thickness or refractive index of the binding layer, are changed, and thus a surface plasmon resonance condition is changed.

FIG. 2 shows a binding curve appearing in the process of the samples 32 being bound to the thin metal film 20 and a dissociation curve appearing in the process of the samples 32 being dissociated from the thin metal film 20. In FIG. 2, a rise in the association rate constant ka means that fast absorption of the bio materials, and a fall in the dissociation rate constant kd means that the bio materials are slowly dissociated. In other words, a dissociation constant $K_D = k_d/k_a$ of an equilibrium state can be found by measuring the association rate constant and the dissociation rate constant. For example, it can be determined whether a small molecular and new medicine candidate material that can be used as a carcinogenic agent can be used as a new medicine by measuring a characteristic that the small molecular and new medicine candidate material is bound to or dissociated from protein including cancer risk factors.

Next, the reflected light including optical data, such as that described above, is detected by the photodetector 70 via the prism 10 and the analyzer 60. Here, the photodetector 70 can find the binding and dissociation kinetics of molecular interactions of the samples 32 by measuring a change in the polarized components of the reflected light (that is, the intensity of the reflected light).

Problems of the conventional SPR sensor for analyzing bio materials are described below with reference to FIGS. 3 and 4. FIG. 3 is a graph showing the measurement of the ellipsometric constant Ψ using the SPR sensor, which shows a similar characteristic to the conventional reflectivity. As shown in FIG. 3, the thin metal film 20 was formed of a thin Au film of 50 nm in thickness, and the light source 40 having a wavelength of 633 nm was used. Furthermore, a binding layer was measured 0 nm and 1 nm in thickness. Furthermore, the binding layer was measured 1.45 in the refractive index n, and the buffer solution 34 was measured 1.333 and 1.334 in the refractive index n.

In the principle of the conventional SPR sensor, the amount of a shift in the SPR angle according to time, showing a minimum reflectivity, is measured by measuring the reflectivity or the ellipsometric constant $\Psi$ from which a change in the intensity of reflected light can be known. Here, if the surface plasmon resonance phenomenon is satisfied, the reflectivity or the ellipsometric constant $\Psi$ has a minimum value, and the SPR angle is near 59° as shown in FIG. 3. It can also be seen that the ellipsometric constant $\Psi$ moves to the right with an increase of the thickness of the binding layer and also a rise in the refractive index of the buffer solution 34. FIG. 3 shows a comparison of a case in which bio materials having a refractive index of 1.45 bound about 1 nm and a case in which there was no binding of bio materials and there was a change in the SPR angle when only the refractive index of the buffer solution 34 was changed from 1.333 to 1.334. From FIG. 3, it can be seen that the two cases show a similar change in the SPR angle. In other words, only pure binding and dissociation characteristics from which a change in the reflective index of the buffer solution has been removed must be measured, but it can be seen that when the binding and dissociation characteristics of bio materials are measured, a problem arises in the measurement results because of a change in the reflective index of the buffer solution.

FIG. 4 is a diagram illustrating a conventional problem in which the binding and dissociation kinetics inherent in samples, appearing in a process of the samples being bound and dissociated, and a change in the refractive index resulting from a buffer solution are mixed together. FIG. 4 is a graph showing the binding and dissociation concentrations inherent in the samples 32 appearing in the binding and dissociation process. FIG. 5 is a graph showing a change in the measurement results of the SPR sensor resulting from a change in the reflective index of the buffer solution 34. FIG. 6 is a graph showing the binding and dissociation concentrations of the samples 32, measured by the SPR sensor, in the state in which the binding concentration inherent in the samples 32 and a change in the refractive index resulting from the buffer solution 34 are mixed together. That is, the samples 32 are very sensitive to effects (indicated by arrows) according to a change in the reflective index of the buffer solution 34, and thus the binding and dissociation concentrations of only pure samples 32 do not clearly appear. Accordingly, it is difficult to calculate the binding and dissociation concentrations of the samples 32 by analyzing the binding and dissociation concentrations of only pure samples 32.

On the other hand, in order to correct a change in the reflective index of the buffer solution 34 and to prevent errors resulting from diffusion between the samples 32 and the buffer solution 34, a correction method using an elaborate valve apparatus and an elaborate air injection apparatus and two or more channels used as a reference channel is being used. However, this method is difficult to distinguish a change in the SPR angle resulting from a change in the reflective index of the buffer solution 34 and a change in the SPR angle resulting from pure binding and dissociation characteristics, and the changes can always serve as measurement error factors. Consequently, the conventional SPR sensor has a fundamental problem in measuring the binding and dissociation characteristics of a material having a low molecular weight, such as small molecule, because of the limits of a measurement method, such as that described above.

Furthermore, the conventional SPR sensor requires a high manufacturing cost for the sensor because it uses the thin metal film 20 made of a noble metal, such as gold (Au) or silver (Ag), for surface plasmon resonance. In addition, the thin metal film 20 is problematic in that a refractive index has a severe variation because surface roughness is not uniform according to a manufacturing process and quantitative measurement for bio materials are difficult because of an unstable optical characteristic.

DISCLOSURE OF INVENTION

Technical Problem

Accordingly, the present invention has been made keeping in mind the above problems occurring in the prior art, and an embodiment of the present invention is to provide an apparatus and method for quantifying the binding and dissociation kinetics of molecular interactions, which are not influenced by a change in the reflective index resulting from a buffer solution in a liquid immersion micro flow paths environment and capable of improving measurement sensitivity because a thin metal film having an unstable light characteristic is not used.

Another embodiment of the present invention is to provide an apparatus and method for quantifying the binding and dissociation kinetics of molecular interactions, which are capable of increasing the reliability and efficiency of researches on binding and dissociation kinetics by using a micro flow path structure optimized to analyze small molecular bio materials.

Solution to Problem

According to an embodiment of the present invention, there is provided an apparatus for quantifying binding and dissociation kinetics of molecular interactions, comprising a micro flow path structure 100, comprising a support 110, a substrate 120 formed on the support 110 and made of a semiconductor or dielectric material, a thin dielectric film 130 formed on the substrate 120, a cover unit 140 configured to have an incident window 142 and a reflection window 144 respectively provided on one side and the other side and disposed on the support 110, and micro flow paths 150 formed in the support 110 and between the support 110 and the cover unit 140; a sample injection unit 200 for forming a binding layer 160 of samples on the thin dielectric film 130 by injecting a buffer solution 210, comprising the samples of a bio material into the micro flow paths 150; a polarization generation unit 300 for radiating incident light, polarized through the incident window 142, to the binding layer 160 at an angle of incidence $\theta$ satisfying a p-wave non-reflecting condition; and a polarization detection unit 400 for detecting a change in the polarization of reflected light of the binding layer 160 which is incident through the reflection window 144.

The thin dielectric film 130 comprises a semiconductor oxide film or a glass film made of a transparent material. It is preferred that the thin dielectric film 130 have a thickness of 0 to 1000 nm.

Furthermore, the micro flow path structure 100 comprises a plurality of inflow paths 152 and a plurality of outflow paths 154 formed on one side and the other side of the support 110, respectively, and the micro flow paths 150 of multiples channels configured to have a plurality of barrier ribs 146 formed in the inner face of the cover unit 140 and to connect the inflow paths 152 and the outflow paths 154, respectively.

Furthermore, the micro flow path structure 100 forms the micro flow path 150 of a single channel, and a plurality of different self-assembled monolayers 132 to which the samples are bound can be further formed on the thin dielectric film 130.

Furthermore, each of the incident window 142 and the reflection window 144 of the cover unit 140 has a curved shell form having a predetermined curvature. The incident light and the reflected light are incident on the incident window 142 and the reflection window 144, respectively, at a vertical angle or at an almost vertical angle of the extent that a polarization state of each of the incident light and the reflected light is not greatly changed.

Furthermore, each of the incident window 142 and the reflection window 144 of the cover unit 140 has a flat sheet shape. The incident light and the reflected light can be incident on the incident window 142 and the reflection window 144, respectively, at a vertical angle or at an almost vertical angle of the extent that a polarization state of each of the incident light and the reflected light is not greatly changed.

Furthermore, it is preferred that the cover unit 140 be integrally made of glass or a transparent synthetic resin material.

Furthermore, the binding layer 160 is a multi-layered film, comprising self-assembled monolayers 132 suitable for the bonding characteristics of various bio materials, a fixation material, and various bio materials including small molecules bonded to the fixation material.

Furthermore, the polarization generation unit 300 comprises a light source 310 for radiating predetermined light and a polarizer 320 for polarizing the radiated light. Here, the light source 310 radiates monochromatic light or white light, and it can be a laser or a laser diode having a wavelength-variable structure.

Furthermore, the polarization generation unit 300 can comprise at least one of a collimation lens 330 for providing parallel light to the polarizer 320, a focusing lens 340 for increasing the amount of the incident light by converging the parallel light passing through the polarizer 320, and a first compensator 350 for phase-delaying the polarized components of the incident light. Here, the polarizer 320 and the first compensator 350 can be rotatably configured or can be further equipped with other polarization modulation means.

Furthermore, the polarization detection unit 400 can comprises an analyzer 410 configured to polarize the reflected light, a photodetector 420 configured to obtain pre-determined optical data by detecting the polarized reflected light, and an operation processor 430 electrically connected to the photodetector 420 and configured to induce quantified values based on the optical data. Further, the photodetector 420 can comprise any one of a CCD type solid state array, a photomultiplier tube, and a silicon photodiode. Further, the operation processor 430 induces the quantified values, including a binding concentration, a binding constant, and a dissociation constant of the samples, by finding an ellipsometric constant $\Psi$ or $\Delta$ regarding a phase difference of an ellipsometry.

Furthermore, the polarization detection unit 400 can further comprise at least one of a second compensator 440 for phase-delaying the polarized components of the reflected light and a spectroscope 450 for making spectroscopic the reflected light. Here, the analyzer 410 and the second compensator 440 can be rotatably configured or further equipped with other polarization modulation means.

According to another aspect of the present invention, there is provided a method of quantifying binding and dissociation kinetics of molecular interactions, comprising a first step S100 of a sample injection unit 200 injecting a buffer solution 210, including samples of small molecular bio materials, into micro flow paths 150 of a micro flow path structure 100; a second step S200 of the samples being bound to a thin dielectric film 130 of the micro flow path structure 100, thus forming a binding layer 160; a third step S300 of a polarization generation unit 300 polarizing predetermined light and making the polarized light incident on the binding layer 160 at an angle of incidence to satisfy a p-wave non-reflecting condition through an incident window 142 of the micro flow path structure 100; a fourth step S400 of reflected light of the binding layer 160 being incident on a polarization detection unit 400 through a reflection window 144 of the micro flow path structure 100; and a fifth step S500 of the polarization detection unit 400 detecting a polarization state of the reflected light using an ellipsometry or a reflectometry.

Furthermore, in the first step S100, the buffer solution 210 including the samples of different concentrations is injected into respective micro flow paths 150 of the micro flow path structure 100 including multiple channels.

Furthermore, in the second step S200, the samples are bound to a plurality of different self-assembled monolayers 132 formed on the thin dielectric film 130, thus forming the different binding layers 160.

Furthermore, the fifth step S500 comprises a step of an analyzer 410 polarizing the reflected light, a step of a photodetector 420 obtaining predetermined optical data by detecting the polarized reflected light, and a step of an operation processor 430 inducing quantified values, including a binding concentration, a binding constant, and a dissociation constant of the samples, by finding an ellipsometric constant $\Psi$ or $\Delta$ of the ellipsometry on the basis of the optical data.

Advantageous Effects of Invention

As described above, in accordance with the apparatus and method for quantifying the binding and dissociation kinetics of molecular interactions according to the present invention, a thin dielectric film is used instead of a thin metal film for the binding of samples. Accordingly, the binding and dissociation kinetics inherent in only the samples can be accurately measured almost without the influence of a change in the reflective index resulting from a buffer solution. Furthermore, there is an advantage in that the manufacturing cost can be remarkably reduced by using a substrate and a thin dielectric film made of a cheap semiconductor or dielectric material.

Furthermore, according to the present invention, an ellipsometry and a reflectometry are used in a p-wave non-reflecting condition, and incident light having a high amount of light is provided by using a laser or a laser diode. Accordingly, the signal to noise ratio is increased, thereby enabling high-sensitivity measurement. Furthermore, there are advantages in that when an ellipsometry is used, quantitative measurement using an amplitude ratio $\Psi$ is possible in a p-wave non-reflecting condition and high-sensitivity measurement is possible through the measurement of a phase difference $\Delta$ at an angle other than the p-wave non-reflecting condition.

Furthermore, the micro flow path structure of the present invention includes the micro flow paths optimized for the analysis of small molecular bio materials and a multi-channel or a single channel composed of a plurality of self-assembled monolayers. Accordingly, various experiment conditions in which samples with varying concentrations are injected into the multi-channel micro flow paths or the degree of binding of the self-assembled monolayers is varied can be provided. Accordingly, there is an advantage in that efficiency in the analysis experiment of bio materials can be improved.

Furthermore, the present invention can be used for a variety of industry fields, such as bio, medical treatment, food, and an environment because high-sensitivity measurement for bio materials can be performed in a non-labeling way in a liquid immersion micro flow paths environment.

Although the present invention has been described in connection with some exemplary embodiments, those skilled in the art will appreciate that the present invention can be modified and varied in various forms without departing from the technical spirit of the present invention. It will be evident that all the modifications or variations or both fall within the scope of the appended claims.

BRIEF DESCRIPTION OF DRAWINGS

The above features and other advantages of the present invention will be more clearly understood from the following detailed description taken in conjunction with the accompanying drawings, in which.

Figure 1:
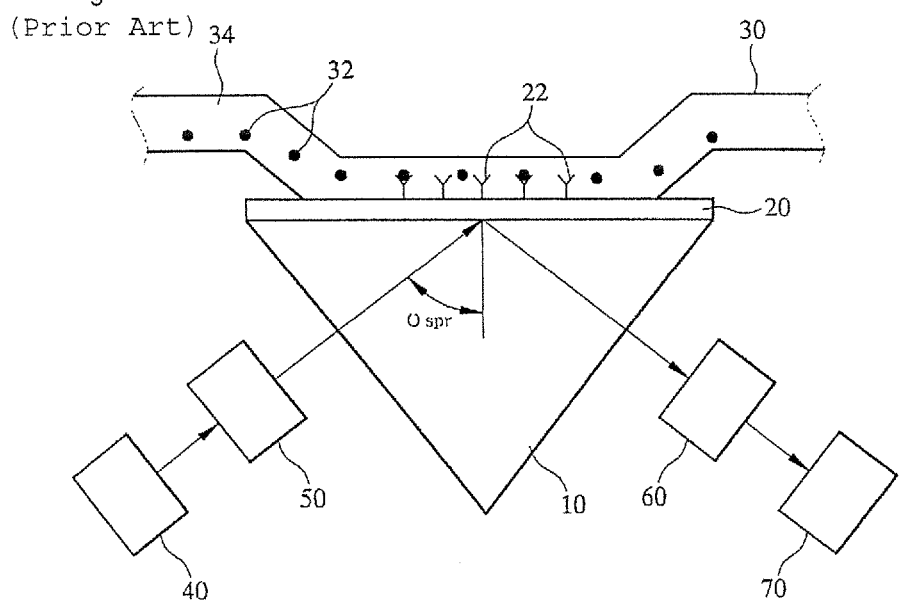
FIG. 1 is a diagram showing the construction of a conventional SPR sensor for analyzing bio materials.
Figure 2:
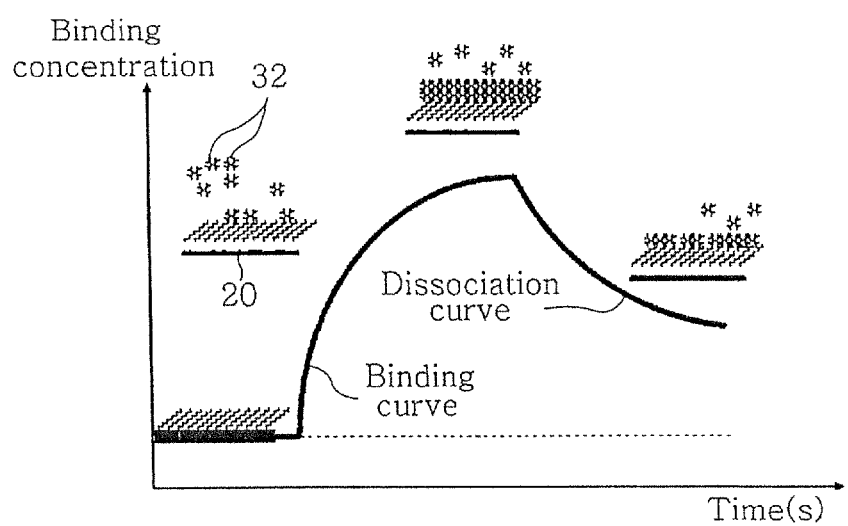
FIG. 2 is a diagram showing a change in the binding concentration in a process of samples being bound to and dissociated from a thin metal film.
Figure 3:
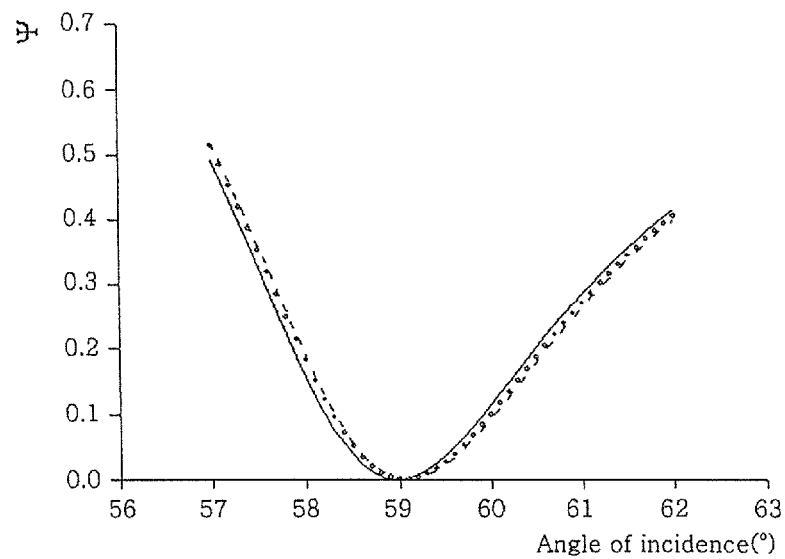
FIG. 3 is a graph showing the measurement results of an ellipsometric constant Ψ using the conventional SPR sensor.
Figure 4:
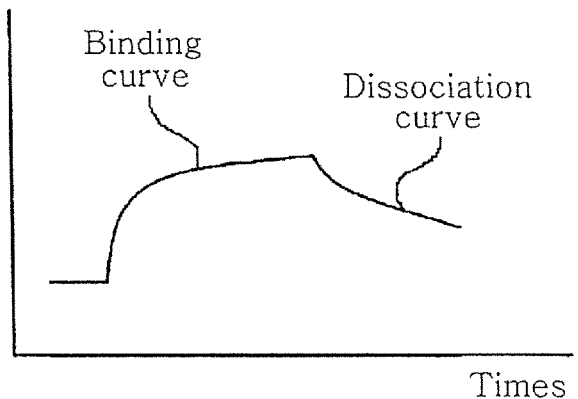
FIGS. 4 to 6 is a diagram illustrating a conventional problem in which the binding and dissociation kinetics inherent in samples, appearing in a process of the samples being bound and dissociated, and a change in the refractive index resulting from a buffer solution are mixed together.
Figure 5:
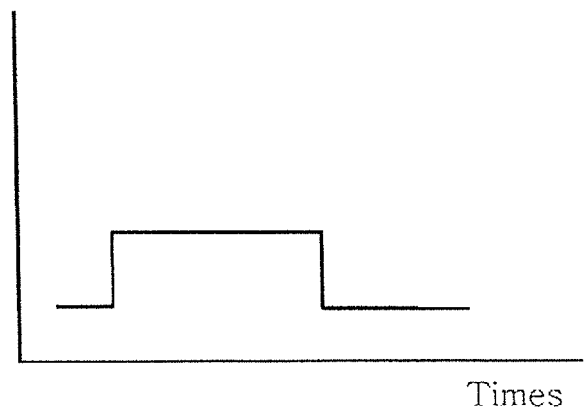
Figure 6:
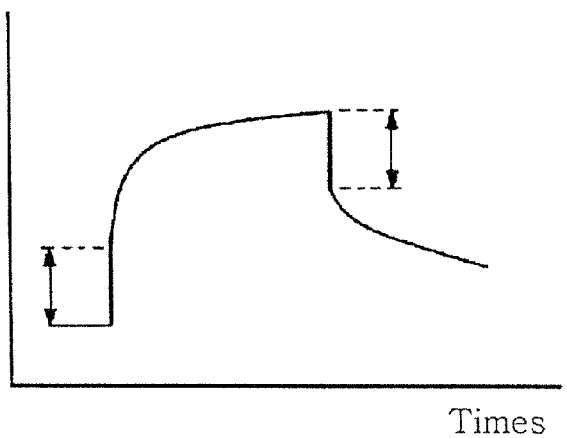

DESCRIPTION OF REFERENCE NUMERALS OF PRINCIPAL ELEMENTS IN THE DRAWINGS 100, 100': micro flow path structure
110: support
112: groove unit
120: substrate
130: thin dielectric film
140: cover unit
132: self-assembled monolayers
142: incident window
144: reflection window
146: barrier ribs
150: micro flow paths
152: inflow paths
154: outflow paths
160: binding layer
200: sample injection unit
210: buffer solution
300: polarization generation unit
310: light source
320: polarizer
330: collimation lens
340: focusing lens
350: first compensator
410: analyzer
400: polarization detection unit
420: photodetector
430: operation processor
440: second compensator
450: spectroscope

MODE FOR THE INVENTION

Hereinafter, some embodiments of the present invention are described in detail with reference to the accompanying drawings. The same reference numerals designate the same elements.

[Construction of an Apparatus for Quantifying Binding and Dissociation Kinetics of Molecular Interactions]

First, the construction of the apparatus for quantifying the binding and dissociation kinetics of molecular interactions according to an embodiment of the present invention is described with reference to the accompanying drawings.

Figure 7:
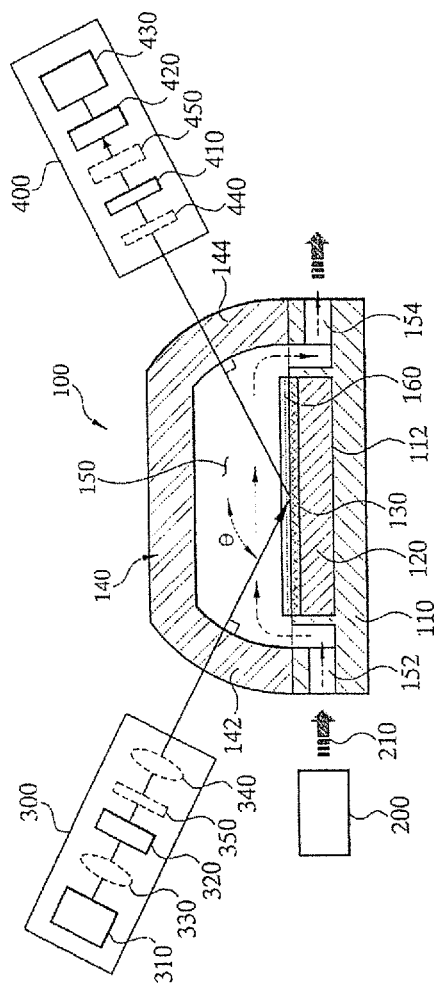
FIG. 7 is a schematic diagram showing the construction of an apparatus for quantifying the binding and dissociation kinetics of molecular interactions according to an embodiment of the present invention.

FIG. 7 is a schematic diagram showing the construction of an apparatus for quantifying the binding and dissociation kinetics of molecular interactions according to an embodiment of the present invention. As shown in FIG. 7, the apparatus for quantifying the binding and dissociation kinetics of molecular interactions according to the embodiment of the present invention chiefly includes a micro flow path structure 100 and a sample injection unit 200, providing a liquid immersion micro flow paths environment, and an optical system, including a polarization generation unit 300 providing incident light and a polarization detection unit 400 detecting a change in the polarization of reflected light.

The present invention is for measuring the binding and dissociation kinetics of bio materials, including small molecules, by using an ellipsometry and a reflectometry. In the apparatus of the present invention, in the sample injection unit 200, a buffer solution 210 including samples (not shown) of bio materials is injected into the micro flow path structure 100. Here, the micro flow path structure 100 can have a micro flow path 150 formed of a multi-channel or a single channel, as described later.

Figure 8:
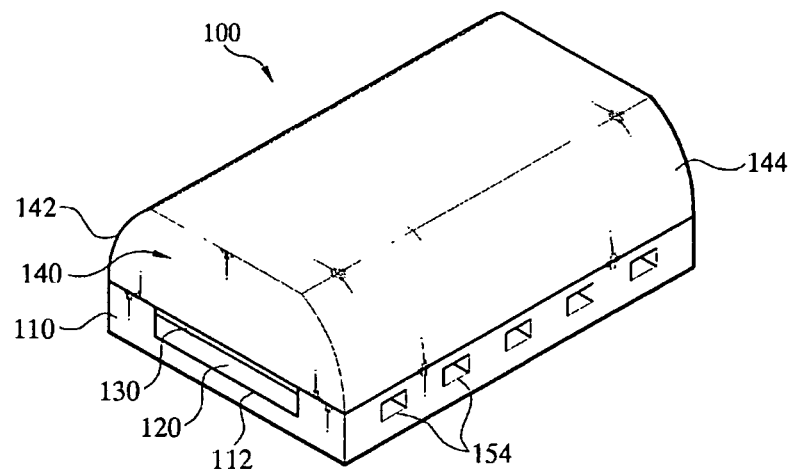
FIG. 8 is a perspective view showing an example of a multi-channel micro flow path structure according to the present invention.
Figure 9:
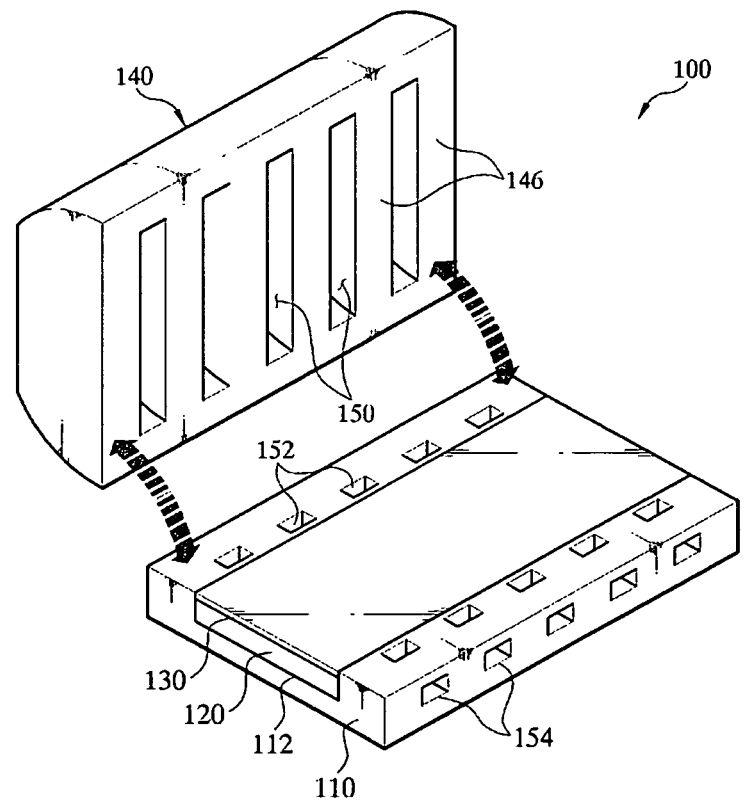
FIG. 9 is an exploded perspective view of the multi-channel micro flow path structure.

FIG. 8 is a perspective view showing an example of a multi-channel micro flow path structure according to the present invention, and FIG. 9 is an exploded perspective view of the multi-channel micro flow path structure. As shown in FIGS. 8 and 9, the micro flow path structure 100 includes a support 110, a substrate 120, a thin dielectric film 130, and a cover unit 140. The micro flow path structure 100 is configured to have a plurality of the micro flow paths 150 form the multi-channel.

The support 110 has a square plate form, as shown in FIG. 9, and has a groove unit 112 formed in the length direction. The substrate 120 and the thin dielectric film 130 are formed in the groove unit 112. Furthermore, the inflow paths 152 and the outflow paths 154 of the micro flow paths 150 are formed on one side and the other side on the basis of the groove unit 112. Here, the groove unit 112, the inflow paths 152, and the outflow paths 154 are formed by using semiconductor etching technology or exposure technology.

The substrate 120 has a square plate form and it is formed in the groove unit 112 of the support 110. According to the present invention, the substrate 120 is made of silicon (Si) which has a complex refractive index of about 4.1285+ i0.0412 at 532 nm and provides stable physical properties with a low cost. However, the substrate 120 can be made of a semiconductor or dielectric material other than silicon (Si).

The thin dielectric film 130 serves to have samples (not shown) of small molecular bio materials bound thereto and dissociated therefrom and to reflect incident light. The thin dielectric film 130 is formed on the substrate 120, as shown in FIG. 9. Here, the thin dielectric film 130 can be made of a transparent and thin film material, including a semiconductor oxide film or a glass film. Furthermore, it is preferred that the thickness of the thin dielectric film 130 be 0 to 1000 nm. On the other hand, the most common example of the thin dielectric film 130 includes a silicon oxide (SiO) film which is grown in thickness of several nano meters by naturally oxidizing silicon (Si). The refractive index of the silicon oxide film is about 1.461 at 532 nm and is very different from the refractive index of the substrate 120 made of silicon (Si). Accordingly, the silicon oxide film helps to increase measurement sensitivity according to the present invention. Furthermore, a glass film made of optical glass can be used as the thin dielectric film 130. The thin dielectric film 130 formed of the silicon oxide film and the glass film can have a constant refractive index, as compared with a thin metal film, such as gold (Au) or silver (Ag). Accordingly, there are advantages in that a stable light characteristic can be provided and the manufacturing cost of the present invention can be reduced.

As shown in FIGS. 7-9, the cover unit 140 is equipped with an incident window 142 and a reflection window 144 provided on one side and the other side, respectively, on the support 110. Here, the incident window 142 and the reflection window 144 are formed in a curved shell form having a predetermined curvature so that incident light and reflected light can be vertically incident on the incident window 142 and the reflection window 144. As shown in FIG. 9, the cover unit 140 is further equipped with a plurality of barrier ribs 146 for forming the micro flow paths 150 of a micro scale. Only the incident window 142 and the reflection window 144 of the cover unit 140 can be made of a transmitting material, such as glass or transparent synthetic resin, but it is preferred that for ease of fabrication, the entire structure of the cover unit 140, including the incident window 142, the reflection window 144, and the barrier ribs 146, be integrally formed by using a molding method. On the other hand, a synthetic resin material can include, for example, acrylic acid resin such as polymethylmethacrylate (PMMA). Silicon (Si)-based materials, such as silicon phosphate polymer (PDMS) and polydimethylsiloxane, can also be used as the synthetic resin material.

The micro flow path 150 is a passage in which the buffer solution 210, including samples, flow and from which the buffer solution 210, including samples, is discharged. A plurality of micro flow paths 150 is formed. That is, since each space between the barrier ribs 146 of the cover unit 140 communicates with the inflow path 152 and the outflow path 154 formed in the support 110 as described above, the plurality of micro flow paths 150 is formed in the micro flow path structure 100. Here, the width of the micro flow paths 150 is a micro scale of 1 mm or less.

Figure 10:
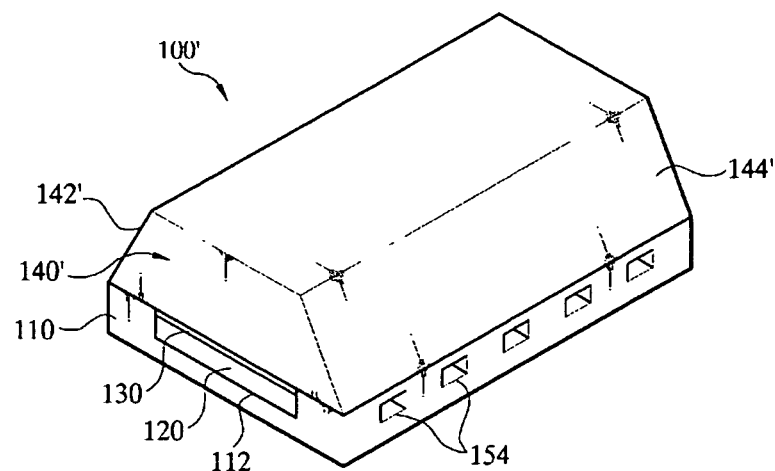
FIG. 10 is a perspective view showing another example of the multi-channel micro flow path structure according to the present invention.

FIG. 10 is a perspective view showing another example of the multi-channel micro flow path structure according to the present invention. As shown in FIG. 10, in a multi-channel micro flow path structure 100', the incident window 142' and the reflection window 144' of a cover unit 140' can have a flat sheet shape. In such a case, the polarization generation unit 300 and the polarization detection unit 400 of FIG. 7 have incident light and reflected light incident on the incident window 142' and the reflection window 144', respectively, at an almost vertical angle of the extent that the polarization state of each of the incident light and the reflected light is not greatly changed or fix the incident light and the reflected light to respective positions where the incident light and the reflected light are vertically incident on the incident window 142' and the reflection window 144', respectively.

Figure 11:
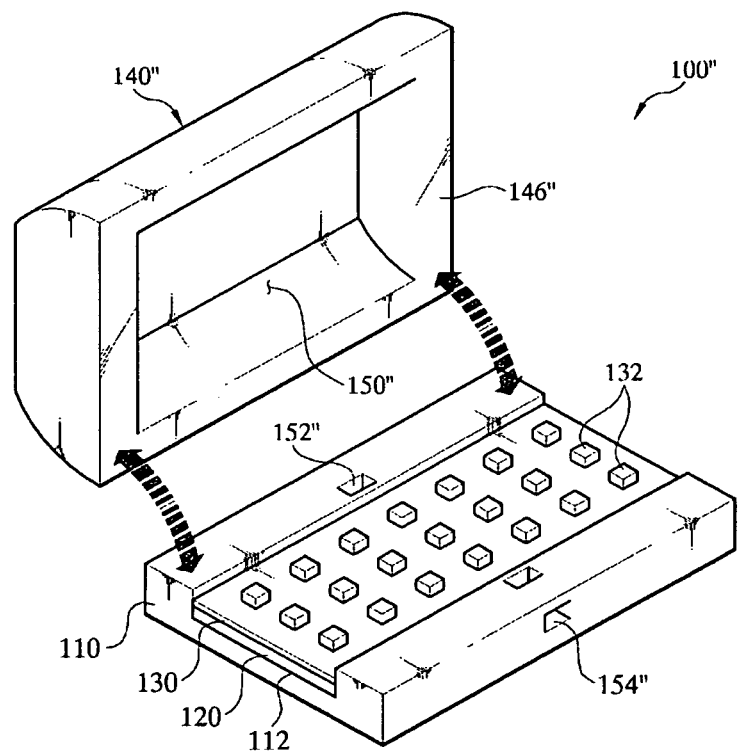
FIG. 11 is an exploded perspective view showing an example of a single channel micro flow path structure according to according to the present invention.

FIG. 11 is an exploded perspective view showing an example of a single channel micro flow path structure according to the present invention. As shown in FIG. 11, a micro flow path structure 100" of a single channel includes one micro flow path 150". That is, the micro flow path structure 100" includes a pair of barrier ribs 146" formed on both ends of a cover unit 140" and one inflow path 152" and one outflow path 154" formed in a support 110, thereby forming the micro flow path 150" of a single channel. Furthermore, a plurality of different self-assembled monolayers (SAM) 132 is formed on a thin dielectric film 130. The self-assembled monolayers 132 are formed of monomers which are composed of a head group and a tail group and voluntarily arranged through a chemical binding method of molecules. Here, each of the self-assembled monolayers 132 can have a different interface characteristic by chemically transforming the function group of the tail group of the self-assembled monolayer 132. That is, each of the self-assembled monolayers 132 has a sensor structure with a different binding and dissociation degree from a sample, and the self-assembled monolayers 132 can measure various binding and dissociation kinetics of bio materials at the same time.

The sample injection unit 200, as shown in FIG. 7, injects the buffer solution 210, including samples (not shown) made of a small molecular bio material, into the inflow paths 152 of the micro flow paths 150. The sample injection unit 200 includes a valve apparatus (not shown) configured to dissolve the samples in the buffer solution 210 at a predetermined concentration and to inject the buffer solution 210 into the micro flow paths 150 or cut the injection of the samples. Here, the sample injection unit 200 can inject the buffer solution 210 into the micro flow path 150 of each channel in the state in which the samples have different concentrations or have a time lag. On the other hand, when the buffer solution 210 is injected into the micro flow paths 150, some of the samples (not shown) are bound on the thin dielectric film 130, thereby forming a binding layer 160 of a predetermined thickness. Here, the binding layer 160 can be a multi-layered film, consisting of the self-assembled monolayer 132 suitable for the bonding characteristic of various bio materials, a fixation material, and various bio materials including small molecules bonded to the fixation material.

The polarization generation unit 300, as shown in FIG. 7, functions to radiate incident light, polarized through the incident window 142 of the micro flow path structure 100 to the binding layer 160. The polarization generation unit 300 can include a light source 310 and a polarizer 320 as essential elements and can further include a collimation lens 330, a focusing lens 340, or a first compensator 350. Here, the polarizer 320 and the first compensator 350 can be rotatably configured or can further include other polarization modulation means. On the other hand, the polarized incident light have p-wave and s-wave polarized components, and light almost close to p waves can be incident on the binding layer 160 in order to increase the signal to noise ratio. In the present invention, incident light has to be radiated at an angle of incidence θ which satisfies a p-wave non-reflecting condition. In an ellipsometry equation, a complex reflection factor ratio can be represented by a ratio of the reflection factor ratio Rp of p waves to the reflection factor ratio Rs of s waves (that is, ρ=Rp/Rs). The p-wave non-reflecting condition refers to a condition in which the reflection factor ratio Rp of p waves has a value close to 0. The p-wave non-reflecting condition is similar to the surface plasmon resonance condition of the conventional SPR sensor and is a condition in which the measurement sensitivity of the present invention is a maximum.

The light source 310 radiates monochromatic light having the same wavelength band as infrared rays, a visible ray, or ultraviolet rays or radiates white light. Various lamps, a light-emitting diode (LED), a laser, or a laser diode (LD) can be as the light source 310. Here, the light source 310 can include a structure capable of varying a wavelength according to the structure of an optical system. On the other hand, the amount of an optical signal of the reflected light can be relatively small near the above-described p-wave non-reflecting condition. In this case, the signal to noise ratio can be raised by radiating light with a high amount of light using a laser or a laser diode (LD), thereby enabling high-sensitivity measurement.

The polarizer 320 includes a polarization plate and polarizes the light radiated by the light source 310. Here, the components of the polarized light include p waves parallel to an incident surface and s waves vertical to the incident surface.

The collimation lens 330 receives the light from the light source 310 and provides parallel light to the polarizer 320. Furthermore, the focusing lens 340 can increase the amount of the incident light by converging the parallel light passing through the polarizer 320. Furthermore, the first compensator 350 functions to phase-delay the polarized components of the incident light.

The polarization detection unit 400, as shown in FIG. 7, functions to receive light reflected by the binding layer 160 through the reflection window 144 and to detect a change in the polarization state of the reflected light. The polarization detection unit 400 includes an analyzer 410, a photodetector 420, and an operation processor 430 (that is, essential elements) and can further include a second compensator 440, and a spectroscope 450. Here, the analyzer 410 corresponds to the polarizer 320 and includes a polarization plate. The analyzer 410 can control the degree of polarization of reflected light or the direction of a polarization surface by polarizing the reflected light again. Furthermore, the analyzer 410 can be rotatably configured according to the structure of an optical system or it can further include polarization modulation means capable of performing functions, such as a phase change or erase of polarized components.

The photodetector 420 functions to obtain optical data by detecting polarized reflected light and to convert the optical data into an electrical signal. Here, the optical data includes information about a change in the polarization state of the reflected light. A CCD type solid state array, a photomultiplier tube (PMT), or a silicon photodiode can be used as the photodetector 420.

The operation processor 430 functions to induce quantified values by acquiring the electrical signal from the photodetector 420. The operation processor 430 has a predetermined interpretation program using a reflectometry and an ellipsometry embedded therein. The operation processor 430 can induce quantified values, such as the binding concentration of samples, and the thickness, binding constant, dissociation constant, and refractive index of the binding layer 160 by extracting and interpreting the optical data converted into the electrical signal. Here, it is preferred that the operation processor 430 induces the quantified values by finding the ellipsometric constant Ψ or Δ regarding a phase difference of an ellipsometry in order to improve measurement sensitivity.

The second compensator 440 functions to control the polarized components of the reflected light through phase delay. The second compensator 440 can be rotatably configured, or it can further include other polarization modulation means.

The spectroscope 450 is used in case where the light source 310 is a light source for white light. The spectroscope 450 makes the reflected light spectroscopic, separates the reflected light having a wavelength of a narrow region, and sends it to the photodetector 420. Here, the photodetector 420 can obtain optical data regarding a distribution of reflected light by using a 2-dimensional image sensor, such as a CCD type solid state array.

[Method of Quantifying the Binding and Dissociation Kinetics of Molecular Interactions]

Hereinafter, the method and principle of quantifying the binding and dissociation kinetics of molecular interactions are described.

Figure 12:
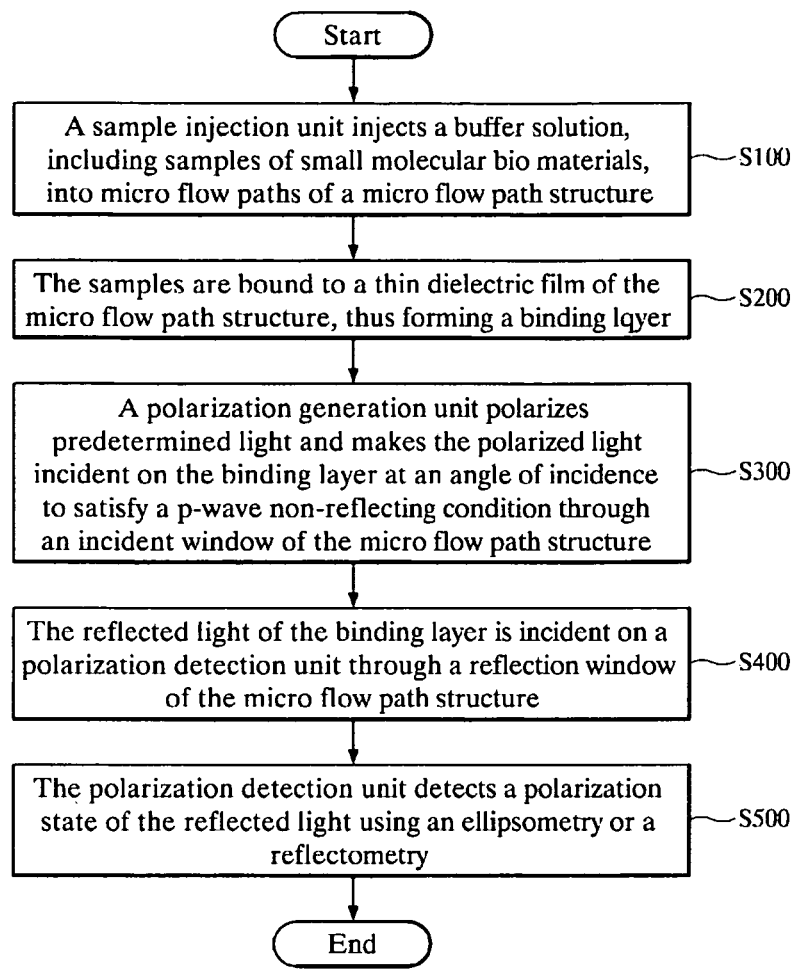
FIG. 12 is a flowchart illustrating a method of quantifying the binding and dissociation kinetics of molecular interactions according to the present invention.

FIG. 12 is a flowchart illustrating the method of quantifying the binding and dissociation kinetics of molecular interactions according to the present invention. As shown in FIG. 12, the quantifying method of the present invention experiences a first step S100 to a fifth step S500.

In the first step S100, as in FIG. 7, the sample injection unit 200 dissolves samples (not shown) of bio materials, including small molecules, in the buffer solution 210 and injects them into the micro flow paths 150 of the micro flow path structure 100. Here, the sample injection unit 200 can inject the buffer solution 210, including the samples of different concentrations, into the respective micro flow paths 150 of multiples channels. Furthermore, the sample injection unit 200 can inject the buffer solution 210 with a time lag for the respective micro flow paths 150. Furthermore, the sample injection unit 200 can inject the buffer solution 210 into some of the micro flow paths 150 and may not use the remaining micro flow paths 150.

In the second step S200, the samples (not shown) of bio materials are bound to the thin dielectric film 130, thus forming the binding layer 160. Unlike the above, the samples can be bound to the plurality of different self-assembled monolayers 132 formed in the micro flow path structure 100" of a single channel shown in FIG. 11, thus forming the binding layer 160 having different bonding characteristics.

In the third step S300, predetermined light radiated by the light source 310 are polarized by the polarizer 320 and then incident on the binding layer 160 through the incident window 142 of the micro flow path structure 100. Here, the polarized incident light has p-wave and s-wave polarized components. On the other hand, the incident light has to have an angle of incidence θ satisfying a p-wave non-reflecting condition.

In the fourth step S400, the reflected light reflected by the binding layer 160 is incident on the polarization detection unit 400 through the reflection window 144 of the micro flow path structure 100. Here, the reflected light is in an elliptically polarized state.

In the fifth step S500, the polarization detection unit 400 detects the polarization state of the reflected light. More particularly, first, the analyzer 410 receives the elliptically polarized reflected light from the binding layer 160 and transmits only light according to a polarization characteristic.

Next, the photodetector 420 obtains predetermined optical data by detecting a change in the polarized components of the reflected light, converts the optical data into an electrical signal, and transmits the electrical signal to the operation processor 430.

Next, the operation processor 430, having a program using a reflectometry or ellipsometry embedded therein, induces quantified values, such as the binding concentration, binding and dissociation constants, and refractive index of the samples by extracting and interpreting the optical data converted into the electrical signal. Here, in the present invention, the operation processor 430 induces the quantified values by finding the amplitude ratio $\Psi$ and the phase difference $\Delta$ of an ellipsometry. The value of the phase difference $\Delta$ has an excellent sensitivity that is 10 times greater than the value of the amplitude ratio $\Psi$, except angles very close to the p-wave non-reflecting angle. Measurement sensitivity can be improved by measuring the value of the phase difference $\Delta$. However, at the p-wave non-reflecting angle, there is almost no change in the phase difference $\Delta$ and the sensitivity of the value of the amplitude ratio $\Psi$ is greatly improved. In particular, a change in the value of the amplitude ratio $\Psi$ at the p-wave non-reflecting angle is advantageous for quantitative measurement because it has a linear change in response to only a change in the thickness or reflective index of a binding material irrespective of the thin dielectric film which is a substrate material.

EXPERIMENT EXAMPLES

Figure 13:
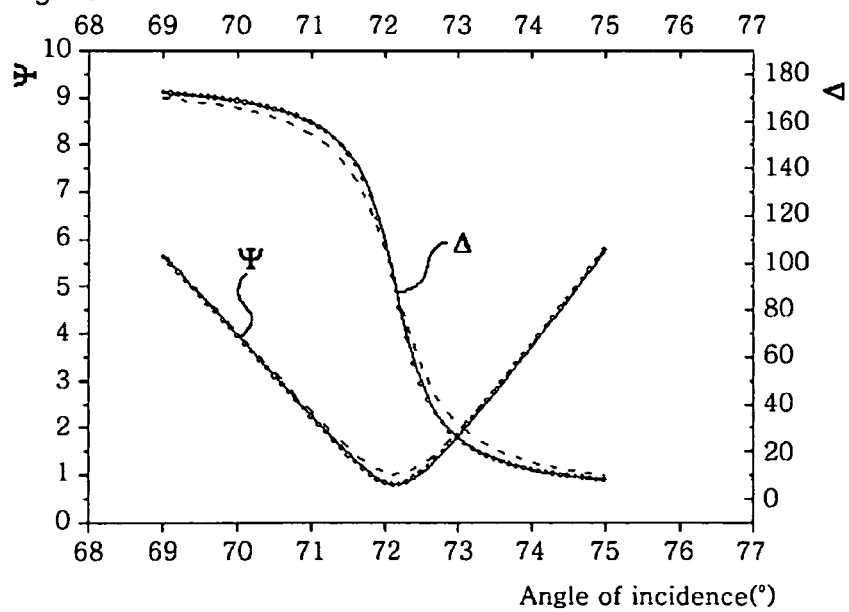
FIG. 13 is a graph showing a change in the ellipsometric constants Ψ and Δ according to a change in the reflective index of a buffer solution in case where a thin dielectric film is formed of a silicon oxide film.

FIG. 13 is a graph showing a change in the ellipsometric constants and according to a change in the reflective index of the buffer solution in case where the thin dielectric film is formed of a silicon oxide film. In FIG. 13, the light source 310 had a wavelength of 532 nm, and a silicon oxide film of 2 nm in thickness was used as the thin dielectric film 130. From FIG. 13, it can be seen that an angle of incidence corresponding to a p-wave non-reflecting condition is around 72 at which the values of the ellipsometric constants $\Psi$ and $\Delta$ are abruptly changed. It can also be seen that in case where the binding layer 160 is not formed (0 nm), there is almost no change in the values of the ellipsometric constants $\Psi$ and $\Delta$ according to a change (1.333, 1.334) in the reflective index of the buffer solution 210. It means that only binding and dissociation kinetics inherent in samples can be measured because the thin dielectric film 130 providing a stable light characteristic is used.

Furthermore, in case where the refractive index of the buffer solution 210 is regular (1.333) and the thickness of the binding layer 160 changes from 0 nm to 1 nm, a change in the value of the amplitude ratio $\Psi$ is sensitive at the p-wave non-reflecting angle, and the sensitivity of the phase difference $\Delta$ is excellent except angles very close to the p-wave non-reflecting angle.

Figure 14:
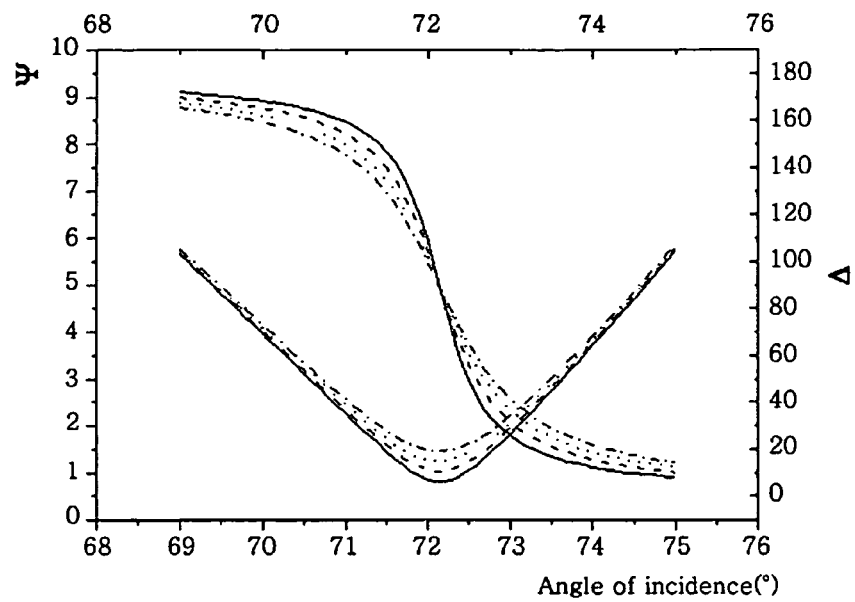
FIG. 14 is a graph showing a change in the ellipsometric constants Ψ and Δ according to a change in the thickness of the binding layer of samples in case where a thin dielectric film is formed of a silicon oxide film.

FIG. 14 is a graph showing a change in the ellipsometric constants $\Psi$ and $\Delta$ according to a change in the thickness of the binding layer of samples in case where the thin dielectric film is formed of a silicon oxide film. FIG. 14 shows a case in which the refractive index of the buffer solution 210 is regular (1.333) and the thickness of the binding layer 160 is 0 nm to 3 nm. From FIG. 14, it can be seen that there is a change in the values of the ellipsometric constants $\Psi$ and $\Delta$ at an angle of incidence around 72° corresponding to the p-wave non-reflecting condition. From FIG. 14, it can be seen that at the p-wave non-reflecting angle, a change in the value of the amplitude ratio $\Psi$ is sensitive and the sensitivity of the phase difference $\Delta$ is excellent except angles very close to the p-wave non-reflecting angle.

Figure 15:
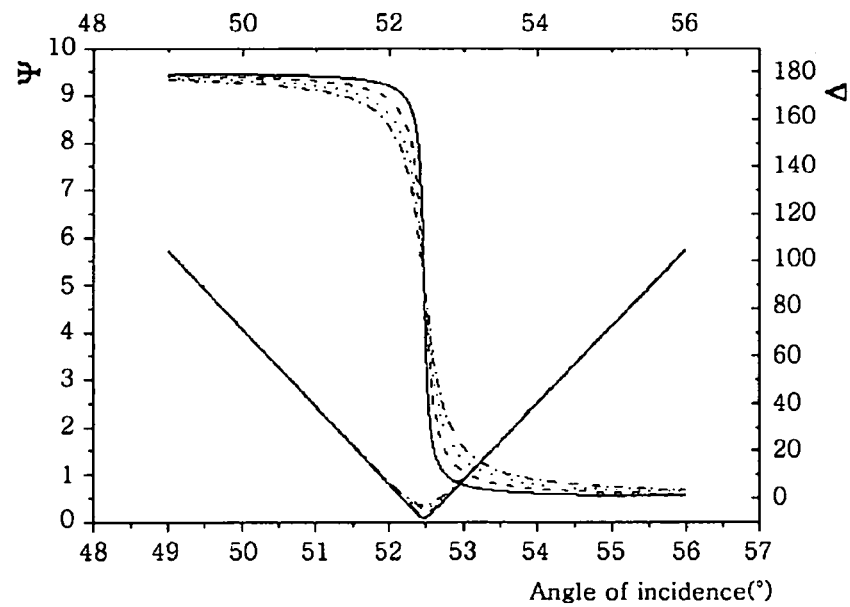
FIG. 15 is a graph showing a change in the ellipsometric constants Ψ and Δ according to a change in the thickness of the binding layer of samples in case where a substrate is made of a glass material.

FIG. 15 is a graph showing a change in the ellipsometric constants $\Psi$ and $\Delta$ according to a change in the thickness of the binding layer of samples in case where the substrate 120 is made of a glass material and the thin dielectric film is not used (0 nm). In FIG. 15, the light source 310 had a wavelength of 532 nm, and a glass film (SF 10) was used as the substrate 120. From FIG. 15, it can be seen that an angle of incidence corresponding to the p-wave non-reflecting condition is around 52.5 at which the values of the ellipsometric constants $\Psi$ and $\Delta$ are suddenly changed. Like the above experiments, it can be seen that the values of the ellipsometric constants $\Psi$ and $\Delta$ are changed according to a change in the thickness of the binding layer 160 (1 nm to 4 nm). Furthermore, from FIG. 15, it can be seen that at the p-wave non-reflecting angle, a change in the value of the amplitude ratio $\Psi$ is sensitive and the sensitivity of the phase difference $\Delta$ is excellent except angles very close to the p-wave non-reflecting angle.

Figure 16:
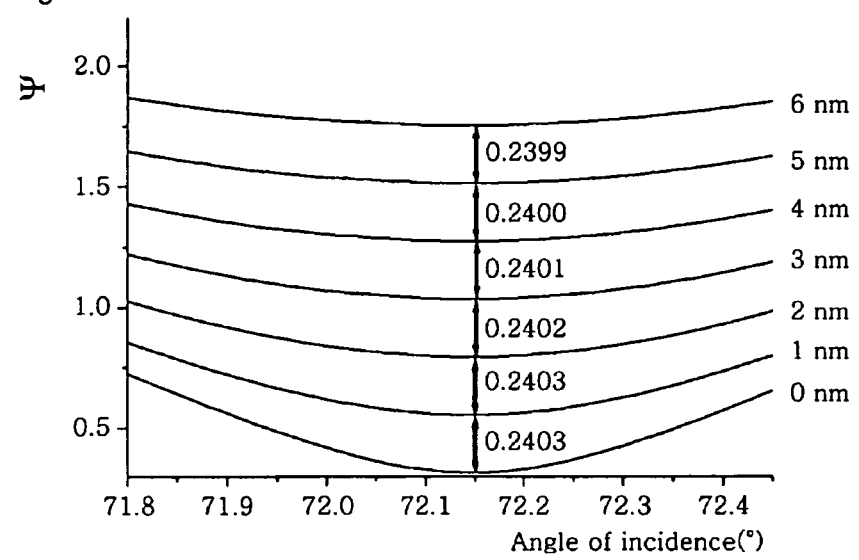
FIG. 16 is a graph showing a change in the ellipsometric constant Ψ according to a change in the thickness of a silicon oxide film or a binding material in case where a substrate is made of silicon (Si).

FIG. 16 is a graph showing a change in the ellipsometric constants $\Psi$ and $\Delta$ according to a change in the thickness of a silicon oxide film or an adsorption material in case where the substrate is made of silicon (Si). From FIG. 16, it can be seen that at the p-wave non-reflecting angle, there is almost no change in the phase difference $\Delta$ and there is a significant change in the value of the amplitude ratio $\Psi$. Here, it can be seen that a change in the value of the amplitude ratio $\Psi$ has a linear change in response to a change in the thickness or reflective index of a thin film bound on a substrate material. If the wavelength of incident light and the refractive index of a medium are known, quantitative measurement is possible on the basis of the value of the amplitude ratio $\Psi$. Accordingly, if the apparatus and method for quantifying the binding and dissociation kinetics of molecular interactions according to the present invention are used, a bio sensor capable of quantitatively analyzing only a change according to only a binding characteristic can be developed unlike the SPR sensor which is sensitive to a change in the surrounding environment.

The invention claimed is:

1. An apparatus for quantifying binding and dissociation kinetics of molecular interactions, the apparatus comprising:
   a micro flow path structure comprising
      a support,
      a substrate on the support and having a semiconductor material,
      a dielectric film on the substrate,
      a cover unit on the support and having an incident window and a reflection window respectively on one side and the other side and,
      said support defining micro flow paths between the support and the cover unit, the micro flow paths comprising a plurality of inflow paths, and a plurality of outflow paths on one side and the other side of the support, respectively,
      the micro flow paths of multiples channels having a plurality of barrier ribs in an inner face of the cover unit and to connect the inflow paths and the outflow paths, respectively;

a sample injection unit for forming a binding layer of samples on the dielectric film by injecting a buffer solution comprising the samples of a bio material into the micro flow paths;

a polarization generation unit for radiating incident light, polarized through the incident window, to the binding layer at an angle of incidence θ satisfying a p-wave non-reflecting condition; and a polarization detection unit for detecting a change in a polarization of reflected light of the binding layer incident through the reflection window;

each of the incident window and the reflection window of the cover unit having a curved shell form;

the incident light and the reflected light being incident on the incident window and the reflection window, respectively, adjacent a vertical angle of the extent that a polarization state of each of the incident light and the reflected light is not greatly changed.

2. The apparatus according to claim 1, wherein the dielectric film comprises at least one of a transparent material semiconductor oxide film and a transparent material glass film.

3. The apparatus according to claim 2, wherein the dielectric film has a thickness of 0 to 1000 nm.

4. The apparatus according to claim 1, wherein the cover unit is integrally made of at least one of glass and a transparent synthetic resin material.

5. The apparatus according to claim 1, wherein the binding layer is a multi-layered film comprising self-assembled monolayers for bonding characteristics of various bio materials, a fixation material, and various bio materials including small molecules bonded to the fixation material.

6. The apparatus according to claim 1, wherein the polarization generation unit comprises a light source for radiating light, and a polarizer for polarizing the radiated light.

7. The apparatus according to claim 6, wherein the light source radiates at least one of monochromatic light and white light.

8. The apparatus according to claim 6, wherein the light source comprises at least one of a laser and a laser diode having a wavelength-variable structure.

9. The apparatus according to claim 6, wherein the polarization generation unit comprises at least one of a collimation lens for providing parallel light to the polarizer, a focusing lens for increasing an amount of the incident light by converging the parallel light passing through the polarizer, and a first compensator 350 for phase-delaying polarized components of the incident light.

10. The apparatus according to claim 9, wherein the polarizer and the first compensator are configured with other polarization modulations.

11. The apparatus according to claim 1, wherein the polarization detection unit comprises:

an analyzer configured to polarize the reflected light;

a photodetector configured to obtain optical data by detecting the polarized reflected light; and an operation processor coupled to the photodetector and generating values based on the optical data.

12. The apparatus according to claim 11, wherein the photodetector comprises at least one of a charge-coupled device (CCD) type solid state array, a photomultiplier tube, and a silicon photodiode.

13. The apparatus according to claim 11, wherein the operation processor generates a binding concentration value, a binding constant value, and a dissociation constant value of the samples, by finding an ellipsometric constant $\Psi$ or $\Delta$.

14. The apparatus according to claim 11, wherein the polarization detection unit further comprises at least one of a second compensator for phase-delaying polarized components of the reflected light, and a spectroscope for making spectroscopic the reflected light.

15. The apparatus according to claim 14, wherein the analyzer and the second compensator are configured with other polarization modulations.

16. A method of quantifying binding and dissociation kinetics of molecular interactions, the method comprising:

using a sample injection unit for injecting a buffer solution including samples of small molecular bio materials into micro flow paths of a micro flow path structure, the buffer solution including the samples of different concentrations and being injected into respective micro flow paths of the micro flow path structure including multiple channels;

binding the samples to a dielectric film of the micro flow path structure for forming a binding layer, the samples being bound to a plurality of different self-assembled monolayers formed on the dielectric film for forming different binding layers;

using a polarization generation unit for polarizing light and making the polarized light incident on the binding layer at an angle of incidence to satisfy a p-wave non-reflecting condition through an incident window of the micro flow path structure;

using reflected light from the binding layer being incident on a polarization detection unit through a reflection window of the micro flow path structure; and using the polarization detection unit for detecting a polarization state of the reflected light using at least one of ellipsometry and reflectometry.

17. The method according to claim 16, wherein the detecting of the polarization state comprises:

using an analyzer for polarizing the reflected light;

using a photodetector for obtaining optical data by detecting the polarized reflected light; and using an operation processor for generating a binding value concentration, a binding constant value, and a dissociation constant value of the samples, by finding an ellipsometric constant $\Psi$ or $\Delta$ of the ellipsometry on the basis of the optical data.

* * * * *